United States Patent [19]
Hu

[11] Patent Number: 5,627,195
[45] Date of Patent: May 6, 1997

[54] TREATMENT FOR OCULAR INFLAMMATION

[75] Inventor: Shixing Hu, Cambridge, Mass.

[73] Assignee: Massachusetts Eye and Ear Infirmary, Boston, Mass.

[21] Appl. No.: 420,244

[22] Filed: Apr. 11, 1995

[51] Int. Cl.$^6$ .................................................. A61K 31/445
[52] U.S. Cl. .......................................... 514/321; 514/912
[58] Field of Search ..................................... 514/321, 912

[56] References Cited

FOREIGN PATENT DOCUMENTS

| | | |
|---|---|---|
| 46-21396 | 6/1971 | Japan . |
| 3-44323 | 2/1991 | Japan . |
| 4-99723 | 3/1992 | Japan . |

OTHER PUBLICATIONS

Marshall, et al. In Vitro Antiplasmodial, Antiamoebic, and Cytotoxic Activities of a Series of Bisbenzylisoquinoline Alkaloids, *Antimicrobial Agents and Chemotherapy*, 38(1):96–103 (1994).

Jigao, et al., Inhibitory Effects of Tetrandrine on Bovine Serum Albumin–Induced Uvetis in Rabbits, *Journal of Ocular Pharmacology*, 9(2):151–156 (1993).

Kondo, et al., Inhibitory Effect of Bisbenzylisoquinoline Alkaloids on Nitric Oxide Production in Activated Macrophages, *Biochemical Pharmacology*, 46(11):1887–1892 (1993).

Xiao, et al., Inhibitory Effect on Tetrandrine on Lens Proteins–Induced Ocular Inflammation in Rabbits *Journal of Ocular Pharmacology*, 8(4):309–315 (1992).

Castranova, et al., Inhibition of Stimulant–Induced Activation of Phagocytic Cells with Tetrandrine *Journal of Leukocyte Biology* 50:412–422 (1991).

Ferrante, et al., Tetrandrine, a Plant Alkaloid, Inhibits the Production of Tumour Necrosis Factor–Alpha (Cachectin) by Human Monocytes, *Clin. exp. Immunol.* 80:232–235 (1990).

Kondo, et al., Inhibitory Effect of Bisbenzylisoquinoline Alkaloids on the Quick Death of Mice Treated with BCG/LPS, *Chem. Pharm. bull.* 38(10):287–2889 (1990).

Ph.D. dissertation of Shixing Hu, Sun Yat–Sen University of Medical Sciences, Guang Zhou, Guang Dong China, 1989.

Seow, et al., In Vitro Immunosuppressive Properties of Teh Plant Alkaloid Tetrandrine, *Int. Archs Allergy appl. Immun.* 85:410–415 (1988).

Rao, et al., Modulation of Lens–Induced Uvetis by Superoxide Dismutase, *Opthlalmic Res.* 18:41–46 (1986).

Albal et al., Clinical Evaluation of Berberine in Mycotic Infections, *Ind. J. Ophthalm.* 34:91–2 (1986).

Mohan, et al., Berberine: An Indigenous Drug in Experimental Herpetic Uveitis, *Ind. J. Ophthalm.* 31:65–68 (1983).

Yao Hsueh Tung Pao 1983; 18:31–36 The Natural Sources and Biological Activities of Bisbenzylisoquinoline (BBI) Alkaloids.

Babbar, et al., Effect of Berberine Chloride Eye Drops on Clinically Positive Trachoma Patients, *Ind. J. Med Res.* 76 (Supp):83–88 (1982).

Sabir, et al., Experimental Study of Antitrachoma Action of Berberine, *Ind. J Med Res* 64(8):1160–1167 (1976).

*Primary Examiner*—Zohreh Fay
*Attorney, Agent, or Firm*—Fish & Richardson P.C.

[57] ABSTRACT

A method of treating a subject with ocular inflammation associated with keratitis or conjunctivitis, which method includes administering to the subject an amount of a pharmaceutical composition containing tetrandrine or a tetrandrine agonist, the amount being effective to reduce the ocular inflammation.

20 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

ATGGCAACTG TTCCTGAACT C                                                         21

( 2 ) INFORMATION FOR SEQ ID NO:2:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

CTTTCTTAGA TATGGACAGG AC                                                    22

( 2 ) INFORMATION FOR SEQ ID NO:3:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GCACAGTGGT GAAAGAGAC                                                        19

( 2 ) INFORMATION FOR SEQ ID NO:4:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

TGCAAGAGTT CCTTGGTGT                                                        19

( 2 ) INFORMATION FOR SEQ ID NO:5:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

TTCCTCTCTG CAAGAGACT                                                                 19

( 2 ) INFORMATION FOR SEQ ID NO:6:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TCAGGAAGTC TCTCTATGT                                                                 19

( 2 ) INFORMATION FOR SEQ ID NO:7:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

ATGAGCACAG AAAGCATGAT CCGC                                                           24

( 2 ) INFORMATION FOR SEQ ID NO:8:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CTCAGGCCCG TCCAGATGAA ACC                                                            23

( 2 ) INFORMATION FOR SEQ ID NO:9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CCATCGACAT GGAGCTGGTG                                                                20

( 2 ) INFORMATION FOR SEQ ID NO:10:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TCTCGACGCG AACGTCTCTA                                                                20

TREATMENT FOR OCULAR INFLAMMATION

BACKGROUND OF THE INVENTION

This invention is related to the treatment of ocular inflammation of pathogenic or allergenic origin. For example, allergic conjunctivitis is an atopic phenomenon caused by many common airborne allergens. In contrast to the general population, subjects with allergic conjunctivitis experience itching and burning of the ocular surface when exposed to such allergens. Clinical signs include chemosis, tearing, conjunctival hyperemia, and lid edema. In a second example of inflammation, keratitis can be caused by pathogens such as viruses, bacteria, and fungi. Symptoms of keratitis include pain, vision impairment, tearing, and photophobia. Corneal inflammation is particularly difficult to treat, due to the avascularity of the cornea.

SUMMARY OF THE INVENTION

In general, the invention relates to a method of treating a subject with ocular inflammation associated with keratitis or conjunctivitis. The method includes administering (e.g., topically, orally, subconjunctivally, or intramuscularly) to the subject a composition which contains an amount of tetrandrine or a tetrandrine agonist and a pharmaceutically acceptable carrier, the amount being effective to reduce the inflammation. The pharmaceutical composition may be formulated as a tablet, a capsule, a liquid, ointment, or cream.

The method of this invention can be used to treat keratitis caused by, among others, a virus (e.g., herpes simplex virus, varicella-zoster virus, variola virus, vacceinial virus, adenovirus, measles virus, rubella virus, and mumps virus). Similarly, it can be used to treat conjunctivitis caused by allergens and any other chemical or biological agents.

Other features or advantages of the present invention will be apparent from the following detailed description, and also from the appending claims.

DETAILED DESCRIPTION OF THE INVENTION

Inflammation is a protective response of an injured tissue, which is designed to destroy, dilute, or isolate an injurious agent. Such agents include pathogens, allergens, toxic compounds, acidic or alkali agents, and trauma.

More specifically, inflammatory responses caused by keratitis include irregularity of the corneal epithelium, ulcerative formation, stromal oedema, neovascularization of the cornea, presence of abnormally large numbers of mononuclear leukocytes, neutrophils, or a combination thereof, and an increased serum specific antibody response to a keratitis pathogen. Corneal inflammation, such as that caused by keratitis, also impairs the subject's vision. Inflammatory responses caused by conjunctivitis include edema of the eyelid, conjunctival congestion, redness, itching, and infiltration of abnormal eosinophils and mast cells.

Effective treatment of inflammation includes the reduction of one or more of the inflammatory responses described above. Such reduction can be measured by clinical observation (e.g., edema, see Table 1, Example 1 below), and by several immunohistological or biochemical analyses known by those in the art to be related to inflammation (e.g., migration of mast cells, and mRNA expression).

The method disclosed herein is based, in part, on the discovery that tetrandrine effectively treats ocular inflammation such as that caused by herpes simplex virus 1-induced keratitis in BALB/c mice. Treatment with tetrandrine or its agonists improves the clinical signs of keratitis and down-regulates mRNA gene expression of proinflammatory cytokine IL-1$\beta$ in the corneas of treated mice (see Example 2 below).

In addition, treatment with tetrandrine or its agonists reduces the allergic inflammation of conjunctiva involving subcutaneous tissues of the lids. This reduction, measured clinically and histopathologically, is statistically significant when compared with untreated groups. Tetrandrine suppresses not only the infiltration of eosinophils and mast cells but also degranulation of mast cells which mediate allergic responses. Thus, tetrandrine and its agonists are not only inhibitors of eosinophil and mast cell migration, but also mast cell stabilizers.

It is well known that activated eosinophils and mast cells can produce granule proteins (14 kD, 15 kD, 17 kD, 18 kD, 19 kD, 21 kD and 55 kD), lipid mediators including leukotrines C4, D4 and E4, and histamine. Interleukin 1 (IL-1) is involved in specific and non-specific inflammatory reactions. Both mast cells and eosinophils produce this cytokine (as well as IL-3, IL-5, IL-6, tumor necrosis factor and transforming growth factor). Tetrandrine and its agonists inhibit the synthesis or release of these inflammatory mediators.

The method disclosed herein is effective to treat ocular inflammation caused by many pathogens, substances (e.g. allergens), and environmental conditions (e.g., trauma, degeneration, or vitamin A deficiency). Examples of ocular inflammatory pathogens include (i) viruses such as HSV-1 virus, HSV-2 virus, varicella-zoster virus, variola virus, vacceinial virus, adenovirus, measles virus, rubella virus, and mumps virus; (ii) bacteria such as Pneumococcus, Pseudomonas, Moraxella (diplobacillus), Streptococcus pyogenes, Klebsiella pneumonieae, Staphylococcus aureus, Staphylococcus epidermidis, Streptococcus viridans, Mycobacterium fortuitum, and Nocardia; (iii) fungi such as Candida, Fusarium, Aspergillus, Penicillium, and Cephalosporium; (iv) Chlamydia; and (v) parasites. Examples of inflammatory substances include acidic or alkali compounds, toxic compounds, or immunogenic agents.

According to the invention, treatment of ocular inflammation caused by any of the above includes administering a composition which includes tetrandrine or a tetrandrine agonist. Tetrandrine, a benzylisoquinoline, was first isolated in 1935 from a Chinese herbal remedy "hanfangchi," the plant *Stephania tetrandra* S. Moore of the Menispermaceae family. *J. Biol Chem.* 109:681–685 (1935). Tetrandrine (6,6',7,12-tetramethoxy-2,2'-dimethylberbaman) was first synthesized in 1968, Inubushi, Y. et al., *Tetra. Lett.* 3399 (1968). Numerous structural analogs of tetrandrine and tetrandrine-like isoquinolines, bisisoquinolines, benzylisoquinolines, and bisbenzylisoquinolines have been isolated or synthesized. Such analogs are examples of tetrandrine agonists. Tetrandrine agonists which can be used to practice the therapeutic method of the present invention include, but are not limited to, those covered by formulas in, or those specifically recited in, the publications set forth below. Likewise, numerous syntheses and methods of isolation of tetrandrine or its agonists are provided in the publications set forth below.

U.S. Pat. No. 2,206,407 (1940)
U.S. Pat. No. 2,248,241 (1941)
Dutcher, *J. Am. Chem. Soc.* 68:419 (1946)
Inubushi, Y. *J. Pharm. Soc. Japan*, 72:220 (1952)
*Chem. Abstr.* 47:6429b (1953)

Bick et al., *Aust. J. Chem.* 9:111 (1956)

*Chem. Abstr.* 51:10113a (1957)

Kametani, Fukumoto, *J. Chem. Soc.*, Suppl. 2, 6141 (1965)

Tomita, et al., *Tetra. Lett.* 1201 (1967)

Inubushi, Y. et al., *Tetra. Lett.* 3399–3402 (1968)

Japanese Pat. No. JP 71 021396B (1971)

Inubushi, Nomura, *Chem. Pharm. Bull.* 25:1636 (1977)

*Great Dictionary of Chinese Materia Medica* (1979)

*Merck Index* (11th ed., 1989)

Japanese Pat. No. JP 3-44323 (1991)

Japanese Pat. No. JP 4-99723 (1992)

Kondo, Y., et al., *Biochem. Pharmacol.* 46:1887–1892 (1993)

Marshall, S. J., et al., *Antimicrobial Agents and Chemotherapy*, 38:96–103 (1994)

*Chem. Abstr.* 120:101957u (1994)

*Chem. Abstr.* 120:270921h (1994)

Tetrandrine, as used in Examples 1 and 2 below, is commercially available (Aldrich, St. Louis, Mo.) and in any event can be isolated or synthesized according to procedures reported in the literature (e.g., see *J. Biol Chem.* 109:681–685, 1935; Merck Index, 11th ed., 1989).

Examples of tetrandrine agonists include: berbamuninum, cepharanthine, cepharanoline, cissampareine, cycleanine, trilobamine, trilobine, dauricine, dauricinoline, dauricoline, daurinoline, epistephanine, epistepharune, fanchinin, fangchinoline, fetidine, hayatidine, hayatine, hayatinine, hernandezine, hernandfoline, hernandine, homoaromoline, homothalicrine, hypoepistephanine, hypoepistephanoline, insulanoline, isochondrodendrin, isoliensinine, isooxyacthine, isotetrandrine, isotrilobine, liensinine, limacine, magnolamine, magnoline, menisarine, menisidine, menisine, (++)-4"O-methylcurine, O-methylthalicberine, neferine, oxyacanthine, stebisimine, stepholine, thalcimine, thalfoetidine, thaliciberine, thalidezine, thalicrine, thalisamine, thalisimine, thalsiminidine, thalmethine dehydrothalisimine, thalphinine, thaipine, 1-bebeerine, cepharanthine, cepharanoline, coclobine, berbamine, tetrandrine methiodide, pycnamine, obamegine, dinklacorine, insularine, aromoline, trigilletimine, cocsoline, cocsuline, cocsuline methiodide, and gilletine. Tetrandrine agonists are structural analogs having the same anti-inflammatory effect as tetrandrine. Tetrandrine agonists include enantiomers, diastereomers, and rotational isomers, where applicable, of the compounds listed above, such as 1-tetrandrine (phaenthine), (R,R) pycnamine, (R,S) obamegine, (R,S) dinklacorine, (R,R) insularine, and (R,S) gilletine.

As shown by the examples above, many tetrandrine agonists have modifications at, for example, the C-1, C-6, C-7, N-2, C'-1, N'-2, C'-6, C'-7, and C'-8 positions. The methyl at N-2 and N'-2 in tetrandrine can be substituted with hydrogen, hydroxy, or a alkyl, or there can be a double bond between N-2 and C-1. The methoxy groups at C-6, C'-6, and C-7 can be each independently substituted with hydrogen, alkyl, alkoxy, hydroxy, or halogen. The (S,S) stereochemistry of chiral carbon atoms C-1 and C'-1 in tetrandrine can each be, independently, S or R The 7',8-oxo linkage in tetrandrine can also be, for example, between C-6' and C-8; in this embodiment, C'-7 is substituted with hydrogen, alkyl, alkoxy, hydroxy, or halogen. In addition, the benzyl groups at C-1 and C'-1 may be linked to each other by an oxo group between the benzyl rings, wherein the oxo group is ortho, meta, or para relative to the methylene of either benzyl group. Each benzyl group may also be independently substituted at one or two positions (such as C-12, C-11, or C-13 or the corresponding C' positions) with hydroxy, amino, halogen, alkyl or alkoxy.

As used herein, alkyl includes branched, straight chain, and cyclic hydrocarbon radicals. Examples of alkyl groups include methyl, ethyl, propyl, isopropyl, cyclopropyl, butyl, isobutyl, sec-butyl, tert-butyl, pentyl, isopentyl, sec-pentyl, tert-pentyl, cyclopenytl, hexyl, and cyclohexyl. The term alkyl include branched, straight chain, and cyclic hydrocarbons as described above that are substituted with one, two, or three halogen atoms. Examples of such haloalkyl groups include trifluoromethyl, chloromethyl, and 2-iodopropyl. Alkoxy includes the corresponding deprotonated alcohol forms of alkyl as defined above. For example, alkoxy includes methoxy, ethoxy, propoxy, isopropoxy, cyclopropoxy, butoxy, and hexyloxy. Halogen includes radicals of fluorine, chlorine, bromine and iodine.

In one aspect, tetrandrine or a tetrandrine agonist is chelated with a metal ion selected from the group of metals consisting of copper, zinc, and magnesium.

Tetrandrine or a tetrandrine agonist is used to treat keratitis or conjunctivitis in subjects, such as mammals and particularly humans. The effective amount of the active compound used to practice the present invention for treating ocular inflammation varies depending upon the manner of administration, the age and body weight of the subject, and the condition of the subject to be treated, and ultimately will be decided by the attending physician or veterinarian. Such amount of the active compound as determined by the attending physician or veterinarian is referred to herein as "effective amount."

Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as flavonoid compounds. Pharmaceutically acceptable salts may be formed, for example, with 1, 2, 3, or more equivalents of hydrogen chloride, hydrogen bromide, and trifluoroacetic acid. Examples of acceptable counter-anions known to those in the art of drug formulation include iodide, iodate, sulfate, carbonate, tartrate, oxalate, acetate, and nitrate. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene. Additional parenteral delivery systems include ethylene/vinyl acetate copolymer particles, osmotic pumps, implantable infusion systems, and liposomes. Formulations for inhalation administration contain lactose, polyoxyethylene-9-lauryl ether, glycocholate, or deoxycholate. A compound of the invention may be administered in unit dosage form, and may be prepared by any of the methods well known in the pharmaceutical art, for example, as described in *Remington's Pharmaceutical Sciences* (Mack Pub. Co., Easton, Pa., 1980). Another aspect of the invention is a packaged drug, containing a pharmaceutical composition formulated into individual dosages and printed instructions for self-administration.

Tetrandrine or a tetrandrine agonist may be prepared for use in parenteral administration, particularly in the form of solutions or liquid suspensions. For example, in certain embodiments, a pharmaceutical composition including tetrandrine or a tetrandrine agonist is administered by intramuscular injection. Tetrandrine or a tetrandrine agonist may also be prepared for oral administration, particularly in the form of tablets or capsules; or intranasal administration, particularly in the form of powders, gels, oily solutions, nasal drops, aerosols, or other liquid formulations. Local administration includes both topical administration (in the form of creams, gels, drops, ointments or other liquid formulations) and administration by local injection. In general, to practice this invention, tetrandrine or its agonist may be provided in an aqueous physiological buffer solution at about 0.01–1.0% w/v (g/ml) for parenteral administration.

The concentration of a disclosed compound in a pharmaceutically acceptable mixture will vary depending on several factors, including the dosage of the compound to be administered, the pharmacokinetic characteristics of the compound(s) employed, and the route of administration. In some embodiments, other specific and non-specific drugs are administered according to factors well-known to those in the art, such as the implicated pathogen, and the general health of the subject. Typical dose ranges are from about 5 to about 50 mg/kg of body weight per day, given in divided doses. Each divided dose may contain the same or different compounds of the invention. The overall dosage will be an effective amount depending on several factors including the overall health of a patient, and the formulation and route of administration of the selected compound(s).

For example, mild keratitis is generally treated with local administration including topical administration (e.g., liquids such as eye drops, ointments, and cream) and subconjunctival injection of a solution of tetrandrine or a tetrandrine agonist. On the other hand, severe keratitis is generally treated with a combined therapy of local administration as above, and systemic administration of tetrandrine or a tetrandrine agonist by oral (e.g. tablets, capsules) or intramuscular routes (e.g., injection, controlled drug release implants).

Without further elaboration, it is believed that one skilled in the art can, based on the description herein, utilize the present invention to its fullest extent. The following specific examples are, therefore, to be construed merely as illustrative, and not limitative of the remainder of the disclosure in any way whatsoever. All publications mentioned herein are hereby incorporated by reference.

EXAMPLE 1

Eighty 8–10 week old female SWR/J mice (Jackson Laboratories, Bar Harbor, Me.) were housed in microisolators within a VR-1 laminar flow isolation unit (Lab Products Inc., BioMedic Corporation, Rochelle Park, N.J.), given mouse chow and water ad libitum, and cared for in accordance with the ARVO Statement for the Use of Animals in Ophthalmic and Vision Research. The animals were divided into four groups of twenty mice: Group 1, normal control (unmanipulated); Group 2, untreated; Group 3, buffered solution (BS)-treated; and Group 4, tetrandrine (TDR)-treated. Tetrandrine was obtained from the Laboratory of Ocular Immunology and Pharmacology, Department of Ophthalmology, Nan Fang Hospital, Guangzhou, China. After conversion to the hydrochloride form, tetrandrine was soluble in water.

Immunization

Short ragweed pollen powder, *Ambrosia artemisiaefolia*, 1.25 mg (International Biologicals, Piedmont, Okla.) was delivered into the nostrils and the conjunctival sac of the right eye of the animals in Group 2, 3 and 4 on days 1 to 5 with an Eppendorf micropipet calibrated to 10 µl. On day 8, the mice were challenged with 1.25 mg of ragweed pollen powder delivered to the conjunctival sac of the right eye. Group 1 animals did not undergo immunization and challenge. The ragweed powder was administered under a laminar flow hood with an Eppendorf micropipet. The tip of the micropipet was introduced in the tube containing ragweed and the powder was aspirated. Then, the tip of the micropipet was placed proximate to eyes of the mouse, and the ragweed was released by pressing the upper part of the Eppendorf micropipet.

TABLE 1

| Group | Scores of Clinical Signs | | |
|---|---|---|---|
| | n | Clinical Scores | P |
| Normal control | 20 | 0 | |
| Untreated | 20 | 3.0 ± 0.7 | |
| BS-treated | 20 | 2.9 ± 0.6 | |
| TDR-treated | 20 | 2.4 ± 0.4 | <0.05* |

*Comparison with the untreated and BS-treated, respectively.

All mice exposed to ragweed (Groups 2–4) developed signs of allergic conjunctivitis, such as conjunctival congestion, redness and edema, after the conjunctival challenge (Table 1). There was no significant difference between BS-treated and the untreated groups (P>0.05). In contrast, the scores of clinical signs of tetrandrine-treated mice were significantly lower than that of the untreated and BS-treated mice (P<0.05).

Histology

After sacrifice (50 mg/mL pentobarbital injection, Nembutal®, Abbott Laboratories, Chicago Ill.), the ocular orbits were exenterated from the mice in Example 1. Orbit samples were processed for light microscopy (LM) by fixation in Karnovsky's solution 1% paraformaldehyde, 1.25% glutaraldehyde, 0.13% sucrose, and 25 mM sodium phosphate in 150 mM sodium cacodylate buffer for 24 h, dehydrated through a graded series of ethanol/water solutions, and embedded in glycol methacrylate (Historesin, Reichert-Jung, Heidelberg, Germany) using an LKB ultra-processor (LKB-producer AB, Bromma, Sweden). Sections (2.5 µm) were stained with hematoxylin-eosin or alkaline Giemsa for observation of mast cells. An Olympus B-H microscope (Olympus Optical Co. Ltd., Tokyo, Japan) and a micrometer ocular grid were used to evaluate the slides (magnification 400×). Cells in the conjunctival epithelium and the immediate subepithelial region were counted with a 0.25×0.025 mm grid; stomal cells were counted with a 0.25×0.25 mm grid. Three fields were counted for each section.

TABLE 2

| Group | Histopathological Observations[†] | | | |
|---|---|---|---|---|
| | n | Eosinophils | Total Mast | Degranulated Mast |
| Normal | 15 | 1 ± 1 | 7 ± 2 | 1 ± 1 |
| Untreated | 15 | 41 ± 29 | 17 ± 6 | 7 ± 4 |
| BS | 15 | 36 ± 17 | 16 ± 5 | 6 ± 3 |
| TDR | 15 | 23 ± 23* | 12 ± 1* | 2 ± 2* |

[†]Values: Mean of cells/mm$^2$ (±SD)
*Statistical significant differences between TDR-treated and untreated or BS-treated groups (P < 0.05).

The untreated and the BS-treated groups had typical allergic conjunctivitis which was pathologically characterized with large numbers of inflammatory cells in the sub-epithelium and stroma of the conjunctiva as well as in the subcutaneous tissue of the eye lids. The infiltrating cells were mast cells and predominantly eosinophils. The stroma closest to the epithelium exhibited the greatest infiltration of eosinophils. In contrast, the eyes of the tetrandrine-treated mice showed much lower numbers of these inflammatory cells.

Mast cells were present in the tissues of the lid but not in the epithelium of any group. Most mast cells in the eyes of the untreated and BS-treated group were degranulated. The tetrandrine-treated groups showed significantly less mast cell infiltration of the eye, and less degranulation, than did the untreated ($P<0.01$) and BS-treated groups ($P<0.05$).

Cytokine mRNA gene expression

Four conjunctival tissues of each mouse group were harvested under microscope 40 min after challenging at day 8 (post-immunization) for PCR analysis. The mRNA extraction, cDNA synthesis and PCR amplification were performed as previously described. Cai, X. et al., *Invest. Ophthalmol. Vis. Sci.*, 34:3585–3592, 1993. Tissue samples were immersed in RNAzol B solution (Biotex Laboratory, Houston, Tex.) kept at 4° C., followed by homogenization in the solution, extraction with phenol and chloroform, and precipitation with isopropanol, i.e., isopropanol:supernatant=1:1 (v/v). 2.0 µg total RNA was used for synthesis of cDNA. Primer sequences were as follows:

IL-1β:

| Sence | 5'ATGGCAACTGTTCCTGAACTC | (SEQ ID NO:1) |
| Anti-sence | 3'CAGGACAGGTATAGATTCTTTC | (SEQ ID NO:2) |

IL-5:

| Sence | 5'GCACAGTGGTGAAAGAGAC | (SEQ ID NO:3) |
| Anti-sence | 3'TGTGGTTCCTTGAGAACGT | (SEQ ID NO:4) |

PCR was performed with AmpliTaq DNA Polymerase (Boehringer, Indianapolis, Ill.) at 2 units/reaction and 10 µl of cDNA. The total reaction volume was 50 µl in each tube. The tubes were amplified in a Perkin Elmer Thermal cycler model 9600 (Perkins Elmer Cetus, Norwalk, Conn.) with the following profile: 40 cycles at 45 sec at 94° C., 45 sec at 60° C. for IL-1β or 45 sec at 52° C. for IL-5, and 2 min at 72° C.

Analysis after PCR detected no mRNA expression of IL-1β and IL-5 in normal conjunctiva. Comparably intensive IL-1β mRNA gene expression was found in the conjunctiva of the untreated and BS-treated groups. However, in the conjunctiva of the tetrandrine-treated group, there was a striking reduction in mRNA expression of IL-1β. Clearly, tetrandrine significantly inhibited the ragweed-stimulated mRNA gene expression of IL-1β.

The level of mRNA gene expression of IL-5 was lower than the expression of IL-1β in the conjunctiva of untreated and treated groups, which were comparable. Nevertheless, in the tetrandrine-treated group there was a notable reduction in mRNA expression of IL-5.

EXAMPLE 2

Six to eight-week old male BALB/c mice obtained from Jackson Laboratories (Bar Harbor, Me.) were housed and cared for as those in Example 1. Herpes simplex virus 1 (KOS strain) stock was obtained from Dr. David Knipe (Harvard Medical School, Boston). After being grown and passed twice in Vero cell monolayers (ATCC CCL 81, Rockville, Md.) the virus stock was suspended in Eagle's MEM. See, e.g., Foster, C. S., *Eye*, 3:194–203 (1989) and Foster et al., *Trans. Am. Ophthamol. Soc.*, 92:325–350 (1994), tetrandrine was obtained as before; acyclovir (Burroughs Wellcome, Research Triangle Park, N.C.) was freshly dissolved in distilled water as a 1.5% solution.

Inoculation

Mice were anesthetized with 2 mg of intraperitoneal ketamine hydrochloride (Ketalar, Parke-Davis, Morris Plains, N.J.) and 400 µg of xylazine (Rompun, Mobay, Shawnee, Kans.). The right cornea of each mouse was scratched 8 times in a criss-cross pattern with a 25-gauge needle, and 5 µL of HSV1 suspension containing $10^5$ PFU was applied. Twenty-two mice infected with HSV-1 were injected intraperitoneally with distilled water as a control group. Days are counted from the date of infection. Experimental groups of twelve mice each were injected intraperitoneally twice daily as follows:

Group 1 was injected with acyclovir (120 mg/kg) from day 0;

Group 2 was injected with acyclovir (120 mg/kg) from day 7;

Group 3 was injected with tetrandrine (30 mg/kg) from day 0;

and Group 4 was injected with tetrandrine (30 mg/kg) from day 7.

Clinical Scores

Inoculated eyes were observed with an operating microscope for 2 weeks following inoculation. Clinical findings were scored for development of stromal edema and cellular infiltration, corneal neovascularization, and corneal ulceration, on a scale of 0 to 4+.

Sixteen out of 22 inoculated control mice developed herpes simplex-induced keratitis (HSK) (72.7% incidence). In Group 2, acyclovir treatment beginning day 7 resulted in 6 out of 12 mice developing HSK (50% incidence, not significantly different from control, $P>0.05$). In contrast, in Group 4, treatment with tetrandrine beginning day 7 resulted in only 1 out of 12 mice developing HSK (8.5% incidence, $P<0.01$). Acyclovir treatment from day 0 decreased the incidence of HSK in Group 1 to 0% ($P<0.01$; 10 mice), while in Group 3, 5 out of 11 mice developed HSK after treatment with tetrandrine from day 0 (45.4% incidence, not statistically significant from control, $P >0.05$).

Specific Antibody Detection

Specific antibody to HSV-1 was detected in the serum of infected mice by direct ELISA. Titertek microtiter plates (ICN Biomedicals Inc., Horsham, Pa.) were coated overnight at 4° C. with a 0.1 ml solution of HSV-1 (KOS strain) in 50 mM sodium bicarbonate buffer, pH 9.6. After washing 3 times with a solution of 0.05% Tween-20 in 20 mM phosphate-buffered saline (PBS-Tween), the plates were incubated for 2 h at 37° C. with normal rabbit serum diluted in PBS-Tween (pH 7.4). After another series of washes, a 1:4 dilution of either experimental or control mouse serum was added to the wells and incubated for 2 h. After washing the plates 3 times, a 1:5000 dilution of peroxidase F(ab')2 rabbit anti-mouse IgG (Jackson ImmunoResearch, West Grove, Pa.) was added to each well and the plates were incubated for 2 h. After a final series of washes, o-phenylene diamine (Sigma Chemical Co., St. Louis, Mo.) was added as a peroxidase substrate to each well (0.1 ml of 0.033% in 0.02M disodium hydrogen phosphate, w/v). After allowing the color reaction to develop for 30 min, the reaction was stopped by the addition of 2 N sulfuric acid, and the absorbance was measured at 492 nm using a Titertek multiscan plate reader (Labsystem, Helsinki, Finland). The specific antibody response to HSV-1 is shown below:

TABLE 3

| | *Antibody Response to HSV-1 |
|---|---|
| Control | 1.184 ± 0.678 OD |
| Group 3 | 0.726 ± 0.130 OD (P < 0.01) |
| Group 4 | 0.827 ± 0.295 OD (P < 0.05) |

*The antibody response of mice treated with acyclovir was significantly reduced as well.

Histology

Mice were sacrificed by carbon dioxide inhalation on day 14 after corneal challenge. The inoculated eyes were enucleated, fixed in Karnovsky's fixative, and embedded in LKB Historesin (LKB Prodicker AB, Bromma, Sweden). Sections (2.5 μm) were prepared with a Sorvall JB-4 microtome and stained with hematoxylin-eosin. In the control group, the inflammatory reaction was evidenced by large numbers of mononuclear leukocytes and neutrophils in both the corneal lesion and in the anterior chamber. The eyes from Group 1 showed no inflammatory reaction, but the eyes from Group 2 exhibited obvious stromal keratitis, as did the eyes from Group 3. The eyes from Group 4 showed a significantly smaller presence of mononuclear leukocytes and neutrophils than Groups 2 and 3.

Cytokine mRNA Gene Expression

Total RNA was extracted from corneas according to Cai, X., et al., *Invest. Ophthalmol. Vis. Sci.*, 34:3585–92 (1993). Corneas of each group were harvested under microscope at day 14 post infection, homogenized in RNAzol B solution Biotex Laboratory, Houston, Tex.), extracted with phenol and chloroform, and precipitated with isopropanol (1:1, v/v). RNA pellets were washed with 75% ethanol, air-dried, and dissolved in distilled water. The samples were stored at −70° C. prior to cDNA synthesis.

Two micrograms of total RNA was denatured for 10 min at 70° C. and incubated at 37° C. for 1 h in a total volume of 20 μL with 0.5 mM oligo (dT) primers, 0.5 mM of each deoxynucleotide triphosphate, 50 mM Tris-HCl (pH 8.3), 10 mM $MgCl_2$, 20 U RNAsin (Promega, Madison, Wis.), and 2.5 U avian myeloblastosis virus reverse transcriptase (BRL, Gaithersburg, Md.). The mixture was brought to 30 μL with distilled water at the end of the incubation.

Sequence specific primers for each cytokine were synthesized by using the phosphoramidite method in an automated DNA synthesizer and purified by using Sephadex NAP-10 columns (both from Pharmacia, Piscataway, N.J.). The oligonucleotide primer sequences were based on the published sequence in the Gene Bank. The sequences and expected amplified PCR product (in base pairs, or BP) are listed in Table 4.

Following the reverse transcription of total RNA into cDNA, PCR was performed by using a wax pellet hot-start technique with slight modifications. Briefly, the lower reagent mix of the PT-PCR reaction contained a final concentration of 12.5 mM Tris-HCL pH 8.3, 62.5 mM KCl (10×PCR Buffer II) (Perkin Elmer, Norwalk, CT), 2.5 mM $MgCl_2$, 200 μM of each dNTP (dATP, dCTP, dGTP, and dTTP), and 20 pmol of each primer. An AmpliWax™ PCR Gem 100 (Perkin Elmer) was added to each tube. All the tubes were incubated at 80° C. for 5 min and cooled to 4° C. The upper reagent mix contained a final concentration of 12.5 mM Tris-HCl pH 8.3; 62.5 mM KCl (10×PCR Buffer II) (Perkin Elmer), AmpliTaq DNA Polymerase (Boehringer) at 2 units/reaction and 10 μL of cDNA. The total reaction volume was 50 μL in each tube. The tube was amplified in a Perkin Elmer Thermal cycler model 9600 (Perkin Elmer Cetus, Norwalk, Conn.) with the following profile: 40 cycles of 45 sec at 94° C., 45 sec at 60° C., and 2 min at 72° C.

Messenger RNA expression of all observed cytokines was not found in normal corneas. Strong expression of mRNA for IL-1β and IL-6 in the corneas of infected mice was observed, while mRNA expression of TNF-α and TGF-β was weak. IL-1β mRNA was expressed only in the inflamed corneas of mice in each group. However, IL-6 mRNA was expressed in the corneas of mice with and without HSK. The pattern of TNF-α mRNA expression was similar to that of IL-1β. TGF-β mRNA expression was detected in the corneas of all groups except normal and non-diseased animals in the untreated group. These data demonstrate that local gene expression of IL-1β, IL-6, TNF-α and TGF-β, particularly the former two, mediates the inflammatory process of HSK in BALB/c mice in vivo. Furthermore, it has been shown for the first time that tetrandrine affects (e.g., down-regulates) the gene transcription of inflammatory cytokines.

Example 2 demonstrates that tetrandrine has therapeutic activity against established HSV-1, and strongly suggest that acyclovir has prophylactic rather than therapeutic activity. Thus, tetrandrine is preferable for pathogen-induced keratitis in clinical therapy, where subjects generally seek treatment after immunological and inflammatory responses have been established.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

TABLE 4

Oligonucleotide Primers and PCR Products

| | Sense | Anti-sense | Product |
|---|---|---|---|
| IL-1β | 5'ATGGCAACTGTTCCTGAACTC (SEQ ID NO:1) | 3'CAGGACAGGTATAGATTCTTTC (SEQ ID NO:2) | 563 BP |
| IL-6 | 5'TTCCTCTCTGCAAGAGACT (SEQ ID NO:5) | 3'TGTATCTCTCTGAAGGACT (SEQ ID NO:6) | 432 BP |
| TNF-α | 5'ATGAGCACAGAAAGCATGATCCGC (SEQ ID NO:7) | 3'CCAAAGTAGACCTGCCCGGACTC (SEQ ID NO:8) | 692 BP |
| TGF-β | 5'CCATCGACATGGAGCTGGTG (SEQ ID NO:9) | 3'ATCTCTGCAAGCGCAGCTCT (SEQ ID NO:10) | 355 BP |

What is claimed is:

1. A method of treating a subject with ocular inflammation is associated with keratitis or conjunctivitis, which method comprises administering to the subject an amount of a pharmaceutical composition containing tetrandrine or a tetrandrine agonist, said amount being effective to reduce the inflammation.

2. A method of claim 1, wherein said inflammation is associated with keratitis.

3. A method of claim 2, wherein said composition is administered by subconjunctival injection.

4. A method of claim 2, wherein said composition is administered orally.

5. A method of claim 2, wherein said composition is administered by intramuscular injection.

6. A method of claim 2, wherein said composition is administered topically.

7. A method of claim 2, wherein said composition is formulated as a tablet, a capsule, a liquid, ointment, or cream.

8. A method of claim 2, wherein said composition contains tetrandrine.

9. A method of claim 2, wherein said inflammation is caused by a virus.

10. A method of claim 2, wherein said inflammation is caused by a virus selected from the group consisting of herpes simplex virus, varicella-zoster virus, variola virus, vacceinial virus, adenovirus, measles virus, rubella virus, and mumps virus.

11. A method of claim 10, wherein said composition contains tetrandrine.

12. A method of claim 10, wherein said inflammation is caused by a herpes simplex virus.

13. A method of claim 1, wherein said inflammation is associated with conjunctivitis.

14. A method of claim 13, wherein said composition is administered orally.

15. A method of claim 13, wherein said composition is administered by intramuscular injection.

16. A method of claim 13, wherein said composition is administered topically.

17. A method of claim 13, wherein said composition is formulated as a tablet, a capsule, a liquid, ointment, or cream.

18. A method of claim 13, wherein said composition contains tetrandrine.

19. A method of claim 13, wherein said inflammation is caused by an allergen.

20. A method of claim 19, wherein said composition contains tetrandrine.

* * * * *